United States Patent
Liu et al.

(10) Patent No.: US 9,891,097 B2
(45) Date of Patent: Feb. 13, 2018

(54) BRIGHTNESS CALIBRATION METHOD USED IN OPTICAL DETECTION SYSTEM WITH A PLURALITY OF DIFFUSERS

(71) Applicants: GLOBAL UNICHIP CORPORATION, Hsinchu (TW); TAIWAN SEMICONDUCTOR MANUFACTURING CO., LTD., Hsinchu (TW)

(72) Inventors: Chang-Ming Liu, Hsinchu County (TW); Pi-Tsan Lo, Hsinchu County (TW); Shih-Hua Hsu, Hsinchu (TW); Chien-Hao Lin, Miaoli County (TW); Teng-Hui Lee, Hsinchu County (TW); Tsung-Ju Hsieh, Hsinchu County (TW)

(73) Assignees: GLOBAL UNICHIP CORPORATION, Hsinchu (TW); TAIWAN SEMICONDUCTOR MANUFACTURING CO., LTD., Hsinchu (TW)

(*) Notice: Subject to any disclaimer, the term of this patent is extended or adjusted under 35 U.S.C. 154(b) by 207 days.

(21) Appl. No.: 14/859,354

(22) Filed: Sep. 21, 2015

(65) Prior Publication Data
US 2016/0377477 A1    Dec. 29, 2016

(30) Foreign Application Priority Data
Jun. 26, 2015    (TW) ............................ 104120768 A (51) Int. Cl.
*G01J 1/02*    (2006.01)
*G01J 1/04*    (2006.01)
(Continued)

(52) U.S. Cl.
CPC .......... *G01J 1/0295* (2013.01); *G01J 1/0418* (2013.01); *G01J 1/0474* (2013.01); *G01J 1/08* (2013.01);
(Continued)

(58) Field of Classification Search
CPC .......... G01J 1/0295; G01J 1/0418; G01J 1/08; G01J 1/0474; G01J 1/4228;
(Continued)

(56) References Cited

U.S. PATENT DOCUMENTS

| 6,191,891 B1* | 2/2001 | Pellicori | .................. G01J 1/08 359/364 |
| 2004/0239798 A1* | 12/2004 | Nayar | .................. H04N 5/2355 348/362 |

(Continued)

*Primary Examiner* — Que T Le
*Assistant Examiner* — Jennifer Bennett
(74) *Attorney, Agent, or Firm* — CKC & Partners Co., Ltd.

(57) ABSTRACT

A brightness calibration method used in an optical detection system includes a single source illuminator and a probe card. The single source illuminator is configured to illuminate the probe card. The probe card has a plurality of detection sites. The brightness calibration method includes: sequentially detecting brightness values at the detection sites through one of a plurality of diffusers by a sensing chip; sequentially detecting transparencies of the diffusers at one of the detection sites by the sensing chip; and selecting and respectively disposing the diffusers corresponding to larger ones of the transparencies over the detection sites corresponding to smaller ones of the brightness values, and selecting and respectively disposing the diffusers corresponding to smaller ones of the transparencies over the detection sites corresponding to larger ones of the brightness values.

9 Claims, 5 Drawing Sheets

(51) Int. Cl.
  *G01J 1/08* (2006.01)
  *G01J 1/42* (2006.01)
(52) U.S. Cl.
  CPC ....... *G01J 1/4228* (2013.01); *G01J 2001/083* (2013.01); *G01J 2001/4247* (2013.01); *G01N 2201/0634* (2013.01)
(58) Field of Classification Search
  CPC ............. G01J 2001/4247; G01J 1/0407; G01J 2001/083; G01N 2201/0634
  See application file for complete search history.

(56) References Cited

U.S. PATENT DOCUMENTS

2005/0219365 A1* 10/2005 DiCarlo ................ H04N 1/401
                                                      348/188
2006/0278897 A1* 12/2006 Heller ..................... G01J 1/04
                                                      257/222

* cited by examiner

BRIGHTNESS CALIBRATION METHOD USED IN OPTICAL DETECTION SYSTEM WITH A PLURALITY OF DIFFUSERS

RELATED APPLICATIONS

This application claims priority to Taiwan Application Serial Number 104120768 filed Jun. 26, 2015, which is herein incorporated by reference.

BACKGROUND

Technical Field

The present disclosure relates to a brightness calibration method and an optical detection system.

Description of Related Art

Single source illuminators in conventional optical detection systems usually have problems of uniformity. In a normal way, the intensity at the central region of the light illuminated from a single source illuminator is greater than that at the peripheral region of the light. If a multi-DUT probe card used in a conventional optical detection system, brightness values of light received by the respective detection sites of the probe card might differ from each other. In order to solve such problem, the conventional optical detection system is further equipped with diffusers disposed over the detection sites, so as to homogenize the light.

On the other hand, the respective diffusers perform differently (e.g., on transparency), which depends on the consistency of processes or the deviations among batches. In addition to the uniformity of the light source and the deviations of the diffusers, some boundary criteria may even worsen the differences of the detection results at different detection sites. There is no workable rule to solve this problem currently.

SUMMARY

Accordingly, an aspect of the disclosure is to provide a brightness calibration method and an optical detection system to solve the above-mentioned problems.

The disclosure provides a brightness calibration method used in an optical detection system. The optical detection system includes a single source illuminator and a probe card. The single source illuminator is configured to illuminate the probe card. The probe card has a plurality of detection sites. The method includes: sequentially detecting brightness values at the detection sites through one of a plurality of diffusers by a sensing chip; sequentially detecting transparencies of the diffusers at one of the detection sites by the sensing chip; and selecting and respectively disposing the diffusers corresponding to larger ones of the transparencies over the detection sites corresponding to smaller ones of the brightness values, and selecting and respectively disposing the diffusers corresponding to smaller ones of the transparencies over the detection sites corresponding to larger ones of the brightness values.

In an embodiment of the disclosure, the method further includes: calculating a uniformity ratio of the brightness values; calculating an average transparency of the transparencies; respectively calculating deviation ratios of the transparencies relative to the average transparency; and discarding the diffusers corresponding to the deviation ratios of which absolute values are larger than the uniformity ratio.

In an embodiment of the disclosure, the selecting and respectively disposing of the diffusers further includes: calculating an average brightness value of the brightness values; calculating an average transparency of the transparencies; and selecting and respectively disposing the diffusers corresponding to the transparencies larger than the average transparency over the detection sites corresponding to the brightness values smaller than the average brightness value, and selecting and respectively disposing the diffusers corresponding to the transparencies smaller than the average transparency over the detection sites corresponding to the brightness values larger than the average brightness value.

In an embodiment of the disclosure, the selecting and respectively disposing of the diffusers further includes: calculating an average brightness value of the brightness values; equally dividing the transparencies into M transparency groups arranged in a descending sequence from large to small, wherein M is a multiple of 2; and selecting and respectively disposing the diffusers corresponding to the N-th transparency group of the transparency groups over the detection sites corresponding to the brightness values smaller than the average brightness value, and selecting and respectively disposing the diffusers corresponding to the (N+M/2)-th transparency group of the transparency groups over the detection sites corresponding to the brightness values larger than the average brightness value, wherein N is a positive integer smaller than or equal to M/2.

In an embodiment of the disclosure, the brightness values has a uniformity ratio, and a difference between an upper limit of the N-th transparency group and a lower limit of the (N+M/2)-th transparency group is equal to or smaller than twice as large as the uniformity ratio.

The disclosure further provides an optical detection system. The optical detection system includes a probe card, a plurality of diffusers, and a single source illuminator. The probe card has a plurality of detection sites. The diffusers are respectively disposed over the detection sites, in which the diffusers respectively have a plurality of transparencies. The single source illuminator is configured to illuminate the probe card such that lights illuminating to the diffusers have a plurality of brightness values, respectively. The transparencies of the diffusers corresponding to smaller ones of the brightness values are larger, and the transparencies of the diffusers corresponding to larger ones of the brightness values are smaller.

In an embodiment of the disclosure, the brightness values have a uniformity ratio. The transparencies have an average transparency. Each of the transparency has a deviation ratio relative to the average transparency. Absolute values of the deviation ratios are equal to or smaller than the uniformity ratio.

In an embodiment of the disclosure, the brightness values have an average brightness value. The transparencies have an average transparency. The transparencies of the diffusers corresponding to the brightness values smaller than the average brightness value are larger than the average transparency, and the transparencies of the diffusers corresponding to the brightness larger than the average brightness value values are smaller than the average transparency.

In an embodiment of the disclosure, the brightness values have an average brightness value. The transparencies are equally divided into M transparency groups arranged in a descending sequence from large to small, and M is a multiple of 2. The transparencies of the diffusers corresponding to the brightness values smaller than the average brightness value are within the N-th transparency group of the transparency groups, the transparencies of the diffusers corresponding to the brightness larger than the average brightness value values are within the (N+M/2)-th transparency group of the transparency groups, and N is a positive integer smaller than or equal to M/2.

Accordingly, the brightness calibration method of the disclosure is substantially performed to dispose the diffusers having larger transparencies over the detection sites corresponding to smaller brightness values, and dispose the diffusers having smaller transparencies over the detection sites corresponding to larger brightness values. In other words, the brightness calibration method of the disclosure provides a rule to screen and arrange the diffusers, so as to effectively minimize the uniformity problem of light illuminated from the single source illuminator through a compensation way. Therefore, the optical detection system manufactured according to the brightness calibration method of the disclosure can reduce the detection deviations caused by the uniformity of light, the deviations of the diffusers, and different locations of the detection sites.

It is to be understood that both the foregoing general description and the following detailed description are by examples, and are intended to provide further explanation of the disclosure as claimed.

BRIEF DESCRIPTION OF THE DRAWINGS

The disclosure can be more fully understood by reading the following detailed description of the embodiment, with reference made to the accompanying drawings as follows.

DETAILED DESCRIPTION

Reference will now be made in detail to the present embodiments of the disclosure, examples of which are illustrated in the accompanying drawings. Wherever possible, the same reference numbers are used in the drawings and the description to refer to the same or like parts.

Figure 1:
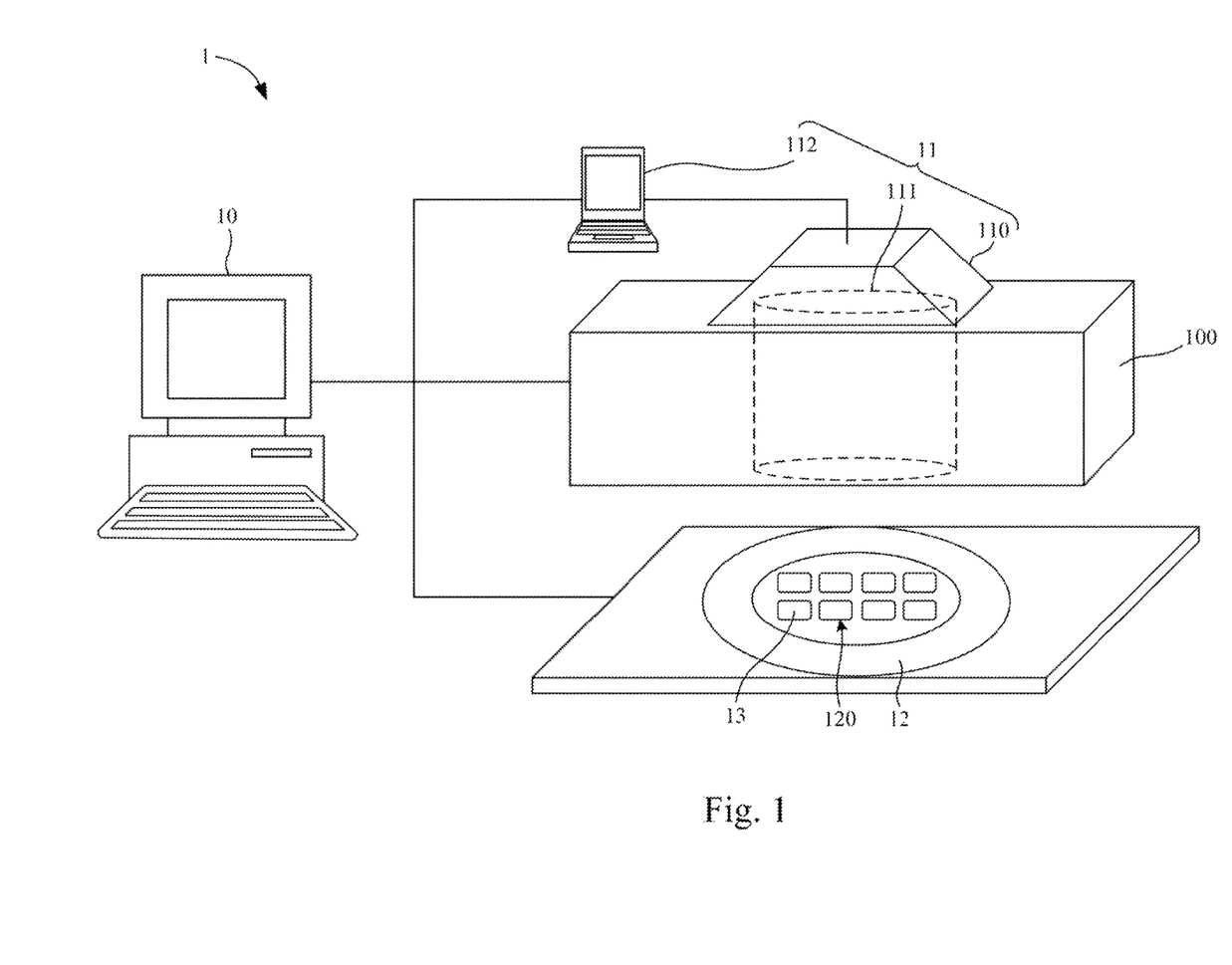
FIG. 1 is a top view of an optical detection system according to an embodiment of the disclosure.

FIG. 1 is a top view of an optical detection system 1 according to an embodiment of the disclosure.

As shown in FIG. 1, in the embodiment, the optical detection system 1 includes a tester host 10, a tester head 100, a single source illuminator 11, a probe card 12, and a plurality of diffusers 13. The probe card 12 has a plurality of detection sites 120, and the diffusers 13 are respectively disposed over the detection sites 120 (i.e., respectively located under the diffusers 13). Each of the detection sites 120 is electrically connected to a sensing chip (not shown), so as to detect electrical or optical properties of the sensing chip. Owing to the uniformity of processes or the deviations among batches, the diffusers 13 respectively have a plurality of transparencies. The single source illuminator 11 includes a light source 110, a lens tube 111, and a light source controller 112. The lens tube 111 is disposed between the light source 110 and the probe card 12, and has at least one lens (not shown) disposed in the tester head 100 and used to convert the point light illuminated from the light source 110 into a surface light as possible. Normally, the light illuminated from the single source illuminator 11 to the probe card 12 has uniformity deviations (e.g., the intensity at the central region of the light is greater than the intensity at the peripheral region of the light), so after illuminated to the probe card 12, the light generates a plurality of brightness values respectively at the diffusers 13. The tester host 10 and the tester head 100 are electrically connected to the single source illuminator 11 and the probe card 12. The tester host 10 is configured to control the light source 110 of the single source illuminator 11 (through the light source controller 112) to illuminate and configured to receive the detection results detected by the probe card 12. Specifically, the optical detection system 1 of the disclosure can be calibrated by performing the brightness calibration method shown in FIG. 2A, so as to reduce the detection deviations caused by the uniformity of light, the deviations of the diffusers, and different locations of the detection sites 120.

Figure 2A:
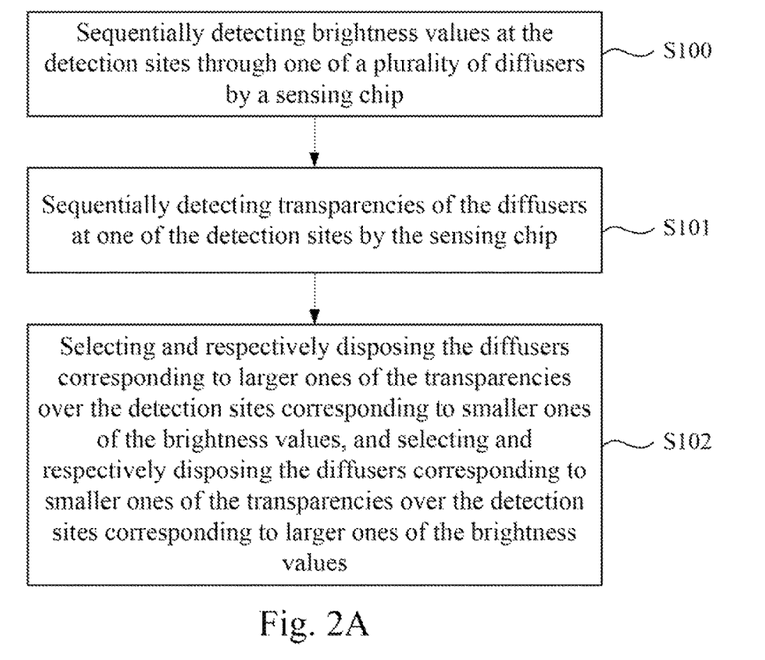
FIG. 2A is a flowchart of a brightness calibration method according to an embodiment of the disclosure.

FIG. 2A is a flowchart of a brightness calibration method according to an embodiment of the disclosure. As shown in FIG. 2A with reference to FIG. 1, the brightness calibration method of the embodiment at least includes steps S100-S102 shown below.

Step S100: sequentially detecting brightness values at the detection sites 120 through one of a plurality of diffusers 13 by a sensing chip.

In the step, a diffuser 13 can be randomly selected from the plurality of diffusers 13, a sensing chip is then used to sequentially detect brightness values at the detection sites 120 through the selected diffuser 13, and finally the detection results can be transferred back to the tester host 10. In order to detect the brightness values at the detection sites 120, the sensing chip is a photosensitive chip.

Step S101: sequentially detecting transparencies of the diffusers 13 at one of the detection sites 120 by the sensing chip.

In the step, a detection site 120 can be selected from the plurality of detection sites 120, and the transparencies of the diffusers 13 can be sequentially detected at the selected detection site 120 by the same sensing chip.

Step S102: selecting and respectively disposing the diffusers 13 corresponding to larger ones of the transparencies over the detection sites 120 corresponding to smaller ones of the brightness values, and selecting and respectively disposing the diffusers 13 corresponding to smaller ones of the transparencies over the detection sites 120 corresponding to larger ones of the brightness values.

Therefore, by performing the step S102, the diffusers 13 having larger transparencies can be corresponded to smaller brightness values and the diffusers 13 having smaller transparencies can be corresponded to larger brightness values, so as to effectively minimize the uniformity problem of light illuminated from the single source illuminator 11 through a compensation way.

On the other hand, as far as the optical detection system 1 is concerned, the light has a plurality of brightness values respectively at the diffusers 13, and the diffusers 13 respectively have the plurality of transparencies. The diffusers corresponding to smaller brightness values have larger transparencies, and the diffusers corresponding to larger brightness values have smaller transparencies.

Figure 2B:
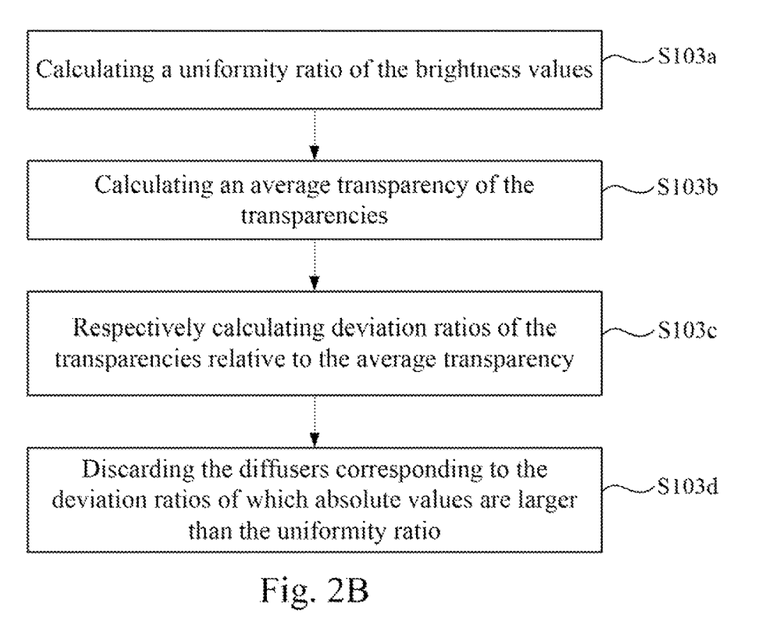
FIG. 2B is a sub-flowchart of a brightness calibration method according to another embodiment of the disclosure.

FIG. 2B is a sub-flowchart of a brightness calibration method according to another embodiment of the disclosure. As shown in FIG. 2A and FIG. 2B, in the embodiment, the brightness calibration method can further includes steps S103a-S103d shown in FIG. 2B between the step S101 and the step S102, and the steps S103a-S103d are shown below.

Step S103a: calculating a uniformity ratio L1 of the brightness values.

In the step, the uniformity ratio L1 is $(B_{max}-B_{min})/(B_{max}+B_{min})$, in which $B_{max}$ is the largest one of the brightness values detected in the step S100, and $B_{min}$ is the smallest one of the brightness values detected in the step S100.

Step S103b: calculating an average transparency $T_{avg}$ of the transparencies.

Step S103c: respectively calculating deviation ratios U1 of the transparencies relative to the average transparency $T_{avg}$.

In the step, the deviation ratio U1 of each of the transparencies relative to the average transparency $T_{avg}$ is $(T-T_{avg})/T_{avg}$.

Step S103d: discarding the diffusers 13 corresponding to the deviation ratios U1 of which absolute values are larger than the uniformity ratio L1.

Figure 3:
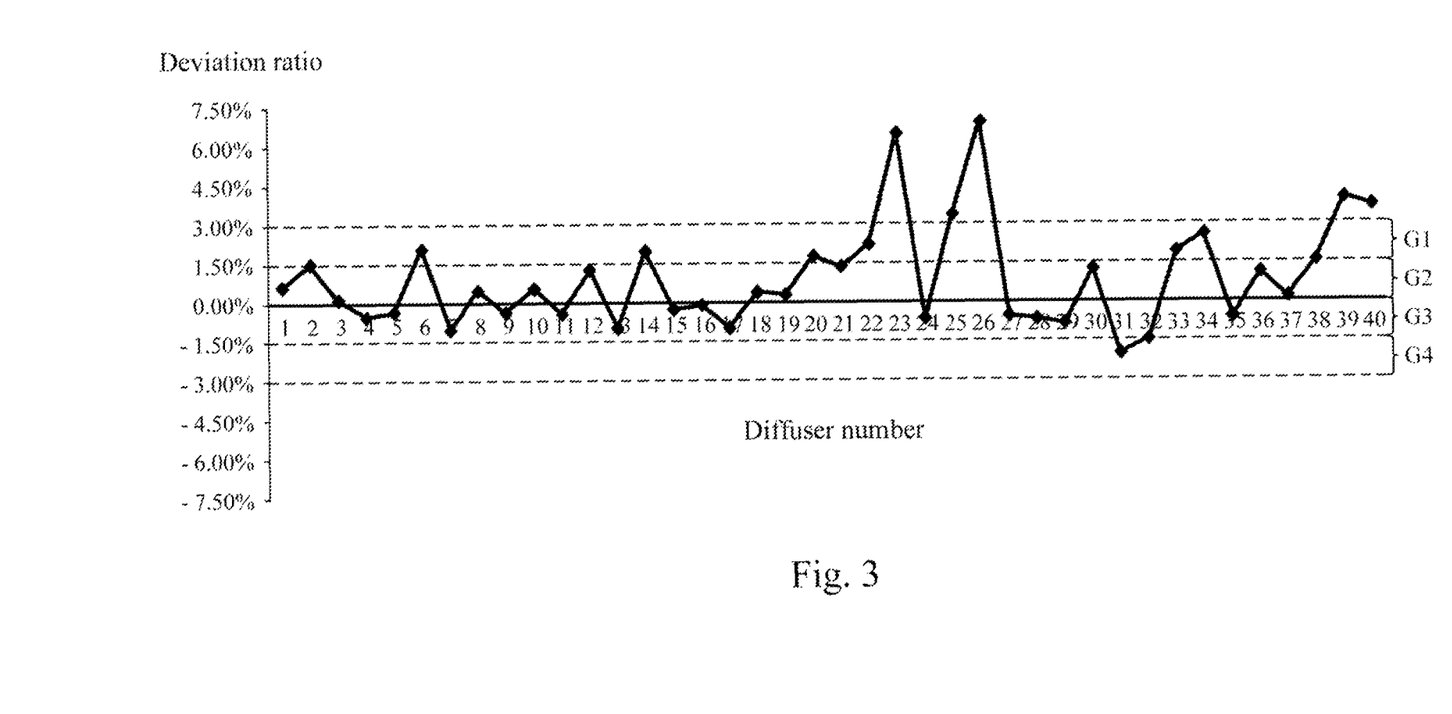
FIG. 3 is a diagram showing deviation ratios of the diffusers derived from the transparencies of the diffusers relative to an average transparency.

FIG. 3 is a diagram showing deviation ratios of the diffusers 13 derived from the transparencies of the diffusers relative to an average transparency. For example, if the uniformity ratio L1 calculated in the step S103a is 3%, the number of the diffusers 13 of which the absolute values of the deviation ratios U1 are larger than the uniformity ratio L1 (i.e., the deviation ratios U1 are larger than 3% or smaller than −3%) are No. 23, 26, 39 and 40, and these diffusers 13 will be discarded in advance according to the step S103d. Therefore, in the subsequent step of selecting and disposing the diffusers 13 (i.e., the step S102), the range of the deviations of the diffusers 13 can match the range of the uniformity of light, so that the selected diffusers 13 will not cause the problem of overcompensation.

On the other hand, as far as the optical detection system 1 is concerned, the brightness values of the light illuminated to the diffusers 13 have a uniformity ratio L2. The transparencies of the diffusers 13 have the average transparency $T_{avg}$. Each of the transparencies has a deviation ratio U2 relative to the average transparency $T_{avg}$, and the absolute values of the deviation ratios U2 are equal to or smaller than the uniformity ratio L2.

Figure 2C:
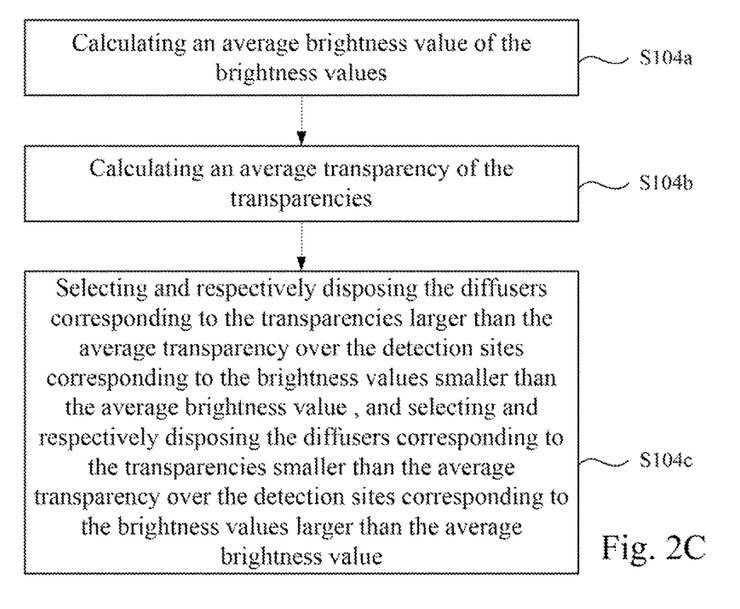
FIG. 2C is a sub-flowchart of a brightness calibration method according to another embodiment of the disclosure.

FIG. 2C is a sub-flowchart of a brightness calibration method according to another embodiment of the disclosure. As shown in FIG. 2A and FIG. 2C, in the embodiment, the step S102 in FIG. 2A can be further replaced by steps S104a-S104c in FIG. 20 shown below.

Step S104a: calculating an average brightness value $B1_{avg}$ of the brightness values.

Step S104b: calculating an average transparency $T_{avg}$ of the transparencies.

Step S104c: selecting and respectively disposing the diffusers 13 corresponding to the transparencies larger than the average transparency $T_{avg}$ over the detection sites 120 corresponding to the brightness values smaller than the average brightness value $B1_{avg}$, and selecting and respectively disposing the diffusers 13 corresponding to the transparencies smaller than the average transparency $T_{avg}$ over the detection sites 120 corresponding to the brightness values larger than the average brightness value $B1_{avg}$.

However, the disclosure is not limited in this regard. In practical applications, the brightness values at the detection sites 120 of the probe card 12 can be further divided into K brightness groups, and the transparencies of the diffusers 13 can also be equally divided into K transparency groups, in which K is an integer larger than 2. Therefore, the detection sites 120 corresponding to the brightness groups arranged in a sequence from dark to bright can be disposed with the diffusers 13 respectively selected from the transparency groups arranged in a descending sequence from large to small.

By performing the foregoing steps S104a-S104c, the diffusers 13 having larger transparencies can be corresponded to smaller brightness values and the diffusers 13 having smaller transparencies an be corresponded to larger brightness values, so as to effectively minimize the uniformity problem of light illuminated from the single source illuminator 11 through a compensation way.

On the other hand, as far as the optical detection system 1 is concerned, the brightness values of the light illuminated to the diffusers 13 have an average brightness value $B2_{avg}$. The transparencies of the diffusers 13 have the average transparency $T_{avg}$. The diffusers 13 having the transparencies larger than the average transparency $T_{avg}$ are corresponded to the brightness values smaller than the average brightness value $B2_{avg}$, and the diffusers 13 having the transparencies smaller than the average transparency $T_{avg}$ are corresponded to the brightness values larger than the average brightness value $B2_{avg}$.

It should be noted that in an embodiment, if the step S103b has been performed between the step S101 and the step S102, the step S104b can be omitted.

Figure 2D:
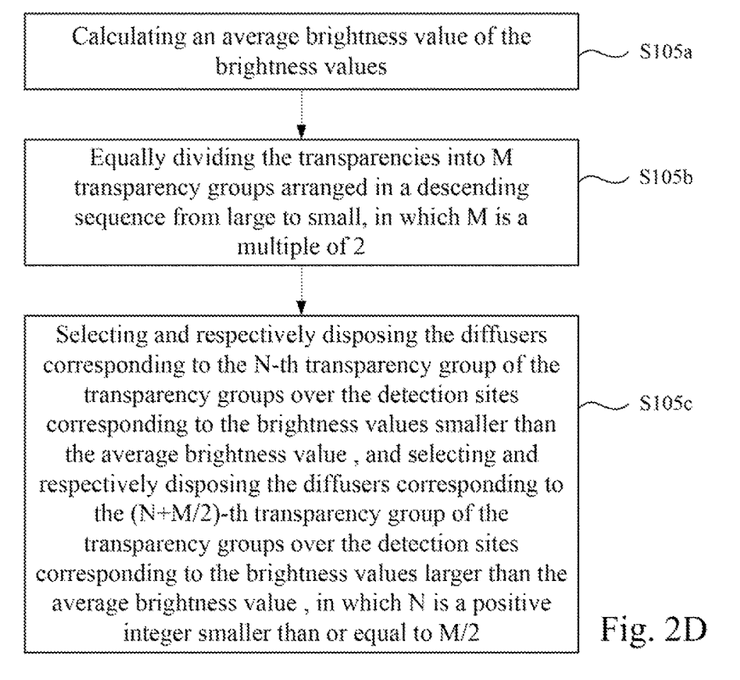
FIG. 2D is a sub-flowchart of a brightness calibration method according to another embodiment of the disclosure.

FIG. 2D is a sub-flowchart of a brightness calibration method according to another embodiment of the disclosure. As shown in FIG. 2A and FIG. 2D, in the embodiment, the step S102 in FIG. 2A can also be further replaced by steps S105a-S105c in FIG. 2D shown below.

Step S105a: calculating an average brightness value $B1_{avg}$ of the brightness values.

Step S105b: equally dividing the transparencies into M transparency groups arranged in a descending sequence from large to small, in which M is a multiple of 2.

In the step, with reference to FIG. 3, the transparencies of the diffusers 13 are equally divided into four transparency groups G1, G2, G3 and G4 arranged in a sequence from large to small, and the range of each transparency group is 1.5%. However, the disclosure is not limited in this regard.

Step S105c: selecting and respectively disposing the diffusers 13 corresponding to the N-th transparency group of the transparency groups over the detection sites 120 corresponding to the brightness values smaller than the average brightness value $B1_{avg}$, and selecting and respectively disposing the diffusers corresponding to the (N+M/2)-th transparency group of the transparency groups over the detection sites 120 corresponding to the brightness values larger than the average brightness value $B1_{avg}$, in which N is a positive integer smaller than or equal to M/2.

Figure 4:
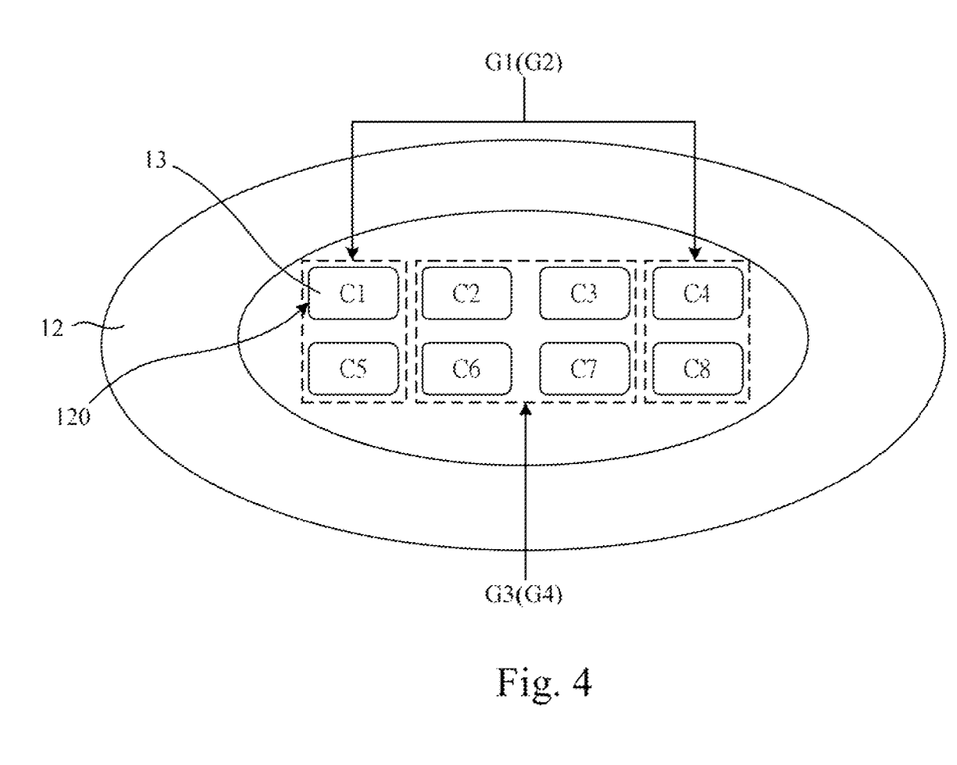
FIG. 4 is a schematic diagram of the probe card in FIG. 1.

FIG. 4 is a schematic diagram of the probe card in FIG. 1. For example, as shown in the figure, in the embodiment, the brightness values of the detection sites 120 at the central region of the probe card 12 (i.e., No. C2, C3, C6 and C7 of the detection sites 120) are larger than the average brightness value $B1_{avg}$, and the brightness values of the detection sites 120 at two sides of the probe card 12 (i.e., No. C1, C4, C5 and C8 of the detection sites 120) are smaller than the average brightness value $B1_{avg}$. According to the step S105c, the detection sites 120 at two sides of the probe card 12 can be respectively disposed with the diffusers 13 selected from the transparency group G1, and the central region of the probe card 12 can be respectively disposed with the diffusers 13 selected from the transparency group G3.

Alternatively, in another embodiment, according to the step S105c, the detection sites 120 at two sides of the probe card 12 can also be respectively disposed with the diffusers 13 selected from the transparency group G2, and the central region of the probe card 12 can also be respectively disposed with the diffusers 13 selected from the transparency group G4.

In an embodiment, a difference between an upper limit of the N-th transparency group and a lower limit of the (N+M/2)-th transparency group is equal to or smaller than twice as large as the uniformity ratio. For example, as shown in FIG. 3, the uniformity ratio L1 is 3%, so the difference between the upper limit and the lower limit of the transparency groups G1-G4 is 6%.

However, the disclosure is not limited in this regard. In practical applications, the brightness values at the detection sites 120 of the probe card 12 can be further divided into K brightness groups, and the transparencies of the diffusers 13 can be equally divided into P transparency groups, in which K is an integer larger than 2, and P is a multiple of K. Therefore, the detection sites 120 corresponding to the brightness groups arranged in a sequence from dark to bright can be disposed with the diffusers 13 respectively selected from the Q-th, (Q+P/k)-th, . . . , and [Q+(K−1)P/K]-th transparency groups arranged in a descending sequence from large to small, in which Q is a positive integer smaller than or equal to P/K.

For example, the detection sites 120 of the probe card 12 can be further divided into three brightness groups, and the transparencies of the diffusers 13 can be equally divided into six transparency groups. Therefore, the detection sites 120 corresponding to the brightness groups arranged in a sequence from dark to bright can be disposed with the diffusers 13 respectively selected from the first, third, and fifth transparency groups arranged in a descending sequence from large to small, or alternatively, disposed with the diffusers 13 respectively selected from the second, fourth, and sixth transparency groups arranged in a descending sequence from large to small.

By performing the foregoing steps S105a-S105c, the diffusers 13 having larger transparencies can be corresponded to smaller brightness values and the diffusers 13 having smaller transparencies can be corresponded to larger brightness values, so as to effectively minimize the uniformity problem of light illuminated from the single source illuminator 11 through a compensation way.

On the other hand, as far as the optical detection system 1 is concerned, the brightness values of the light illuminated to the diffusers 13 have an average brightness value $B2_{avg}$. The transparencies of the diffusers 13 are equally divided into M transparency groups arranged in a descending sequence from large to small, in which M is a multiple of 2. The transparencies of the diffusers 13 corresponding to the detection sites 120 of which the brightness values are smaller than the average brightness value $B1_{avg}$ are within the N-th transparency group of the transparency groups, the transparencies of the diffusers corresponding to the detection sites 120 of which the brightness values are larger than the average brightness value $B1_{avg}$ are within the (N+M/2)-th transparency group of the transparency groups, in which N is a positive integer smaller than or equal to M/2.

According to the foregoing recitations of the embodiments of the disclosure, it can be seen that the brightness calibration method of the disclosure is substantially performed to dispose the diffusers having larger transparencies over the detection sites corresponding to smaller brightness values, and dispose the diffusers having smaller transparencies over the detection sites corresponding to larger brightness values. In other words, the brightness calibration method of the disclosure provides a rule to screen and arrange the diffusers, so as to effectively minimize the uniformity problem of light illuminated from the single source illuminator through a compensation way. Therefore, the optical detection system manufactured according to the brightness calibration method of the disclosure can reduce the detection deviations caused by the uniformity of light, the deviations of the diffusers, and different locations of the detection sites.

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fail within the scope of the following claims.

What is claimed is:

1. A brightness calibration method used in an optical detection system, the optical detection system comprising a single source illuminator and a probe card, the single source illuminator being configured to illuminate the probe card, the probe card having a plurality of detection sites, the method comprising:
   sequentially detecting brightness values at the detection sites through one of a plurality of diffusers by a sensing chip;
   sequentially detecting transparencies of the diffusers at one of the detection sites by the sensing chip; and
   selecting and respectively disposing the diffusers corresponding to larger ones of the transparencies over the detection sites corresponding to smaller ones of the brightness values, and selecting and respectively disposing the diffusers corresponding to smaller ones of the transparencies over the detection sites corresponding to larger ones of the brightness values.

2. The brightness calibration method of claim 1, further comprising:
   calculating a uniformity ratio of the brightness values;
   calculating an average transparency of the transparencies;
   respectively calculating deviation ratios of the transparencies relative to the average transparency; and
   discarding the diffusers corresponding to the deviation ratios of which absolute values are larger than the uniformity ratio.

3. The brightness calibration method of claim 1, wherein the selecting and respectively disposing of the diffusers further comprises:
   calculating an average brightness value of the brightness values;
   calculating an average transparency of the transparencies; and
   selecting and respectively disposing the diffusers corresponding to the transparencies larger than the average transparency over the detection sites corresponding to the brightness values smaller than the average brightness value, and selecting and respectively disposing the diffusers corresponding to the transparencies smaller than the average transparency over the detection sites corresponding to the brightness values larger than the average brightness value.

4. The brightness calibration method of claim 1, wherein the selecting and respectively disposing of the diffusers further comprises:

calculating an average brightness value of the brightness values;

equally dividing the transparencies into M transparency groups arranged in a descending sequence, wherein M is a multiple of 2; and selecting and respectively disposing the diffusers corresponding to the N-th transparency group of the transparency groups over the detection sites corresponding to the brightness values smaller than the average brightness value, and selecting and respectively disposing the diffusers corresponding to the (N+M/2)-th transparency group of the transparency groups over the detection sites corresponding to the brightness values larger than the average brightness value, wherein N is a positive integer smaller than or equal to M/2.

5. The brightness calibration method of claim 4, wherein the brightness values has a uniformity ratio, and a difference between an upper limit of the N-th transparency group and a lower limit of the (N+M/2)-th transparency group is equal to or smaller than twice as large as the uniformity ratio.

6. An optical detection system, comprising:
a probe card having a plurality of detection sites;
a plurality of diffusers respectively disposed over the detection sites, wherein the diffusers respectively have a plurality of transparencies; and
a single source illuminator configured to illuminate the probe card, such that lights illuminating to the diffusers have a plurality of brightness values, respectively,
wherein the transparencies of the diffusers corresponding to smaller ones of the brightness values are larger, and the transparencies of the diffusers corresponding to larger ones of the brightness values are smaller, wherein the brightness values have an average brightness value, the transparencies have en average transparency, the transparencies of the diffusers corresponding to the brightness values smaller than the average brightness values are larger than the average transparency, and the transparencies of the diffusers corresponding to the brightness larger than the average brightness value values are smaller than the average transparency.

7. The optical detection system of claim 6, wherein the brightness values have a uniformity ratio, each of the transparency has a deviation ratio relative to the average transparency, and absolute values of the deviation ratios are equal to or smaller than the uniformity ratio.

8. The optical detection system of claim 6, wherein the transparencies are equally divided into M transparency groups arranged in a descending sequence, M is a multiple of 2, the transparencies of the diffusers corresponding to the brightness values smaller than the average brightness value are within the N-th transparency group of the transparency groups, the transparencies of the diffusers corresponding to the brightness larger than the average brightness value values are within the (N+M/2)-th transparency group of the transparency groups, and N is a positive integer smaller than or equal to M/2.

9. The optical detection system of claim 8, wherein the brightness values has a uniformity ratio, and a difference between an upper limit of the N-th transparency group and a lower limit of the (N+M/2)-th transparency group is equal to or smaller than twice as large as the uniformity ratio.

* * * * *